(12) United States Patent
Linder et al.

(10) Patent No.: US 8,501,416 B2
(45) Date of Patent: Aug. 6, 2013

(54) FLUIDIC STRUCTURES INCLUDING MEANDERING AND WIDE CHANNELS

(75) Inventors: Vincent Linder, Watertown, MA (US); Samuel K. Sia, New York, NY (US); George M. Whitesides, Newton, MA (US); Max Narovlyansky, Cambridge, MA (US); Adam Siegel, Leesburg, VA (US)

(73) Assignee: President and Fellows of Harvard College, Cambridge, MA (US)

( * ) Notice: Subject to any disclaimer, the term of this patent is extended or adjusted under 35 U.S.C. 154(b) by 988 days.

(21) Appl. No.: 11/887,487

(22) PCT Filed: Apr. 19, 2006

(86) PCT No.: PCT/US2006/014583
§ 371 (c)(1),
(2), (4) Date: Feb. 24, 2010

(87) PCT Pub. No.: WO2006/113727
PCT Pub. Date: Oct. 26, 2006

(65) Prior Publication Data
US 2010/0167318 A1      Jul. 1, 2010

Related U.S. Application Data
(60) Provisional application No. 60/672,921, filed on Apr. 19, 2005.

(51) Int. Cl.
*G01N 33/53*         (2006.01)
(52) U.S. Cl.
USPC ............ 435/7.1; 427/2.11; 427/2.13; 427/10; 436/518; 436/523
(58) Field of Classification Search
None
See application file for complete search history.

(56) References Cited

U.S. PATENT DOCUMENTS
4,963,498  A    10/1990   Hillman et al.
5,571,410  A    11/1996   Swedberg et al.
(Continued)

FOREIGN PATENT DOCUMENTS
EP    1 489 303 A2    12/2004
JP    2002-525590 A   8/2002
(Continued)

OTHER PUBLICATIONS
Fujimori, et al., "Gold Colloid Antibody Method: Silver Intensifying Method," *Tissue Cytochemistry*, pp. 120-124 (1996).
(Continued)

*Primary Examiner* — N. C. Yang
(74) *Attorney, Agent, or Firm* — Wolf, Greenfield & Sacks, P.C.

(57) ABSTRACT

The present invention relates generally to microfluidic structures, and more specifically, to microfluidic structures and methods including meandering and wide channels. Microfluidic systems can provide an advantageous environment for performing various reactions and analysis due to a reduction in sample and reagent quantities that are required, a reduction in the size of the operating system, and a decrease in reaction time compared to conventional systems. Unfortunately, the small size of microfluidic channels can sometimes result in difficulty in detecting a species without magnifying optics (such as a microscope or a photomultiplier). A series of tightly packed microchannels, i.e., a meandering region, or a wide channel having a dimension on the order of millimeters, can serve as a solution to this problem by creating a wide measurement area. Although this invention mainly describes the use of meandering and wide channels in heterogeneous immunoassays on a microfluidic chip, this invention could be used for amplifying optical signals for other types of reactions and/or assays.

38 Claims, 9 Drawing Sheets

U.S. PATENT DOCUMENTS

| | | | |
|---|---|---|---|
| 5,637,469 | A | 6/1997 | Wilding et al. |
| 5,866,345 | A | 2/1999 | Wilding et al. |
| 5,957,579 | A | 9/1999 | Kopf-Sill et al. |
| 5,958,694 | A * | 9/1999 | Nikiforov ............... 435/6.12 |
| 5,971,158 | A | 10/1999 | Yager et al. |
| 6,033,546 | A | 3/2000 | Ramsey |
| 6,103,199 | A | 8/2000 | Bjornson et al. |
| 6,146,489 | A | 11/2000 | Wirth |
| 6,186,660 | B1 | 2/2001 | Kopf-Sill |
| 6,214,560 | B1 | 4/2001 | Yguerabide et al. |
| 6,361,958 | B1 | 3/2002 | Shieh et al. |
| 6,479,299 | B1 | 11/2002 | Parce et al. |
| 6,488,872 | B1 | 12/2002 | Beebe et al. |
| 6,488,896 | B2 | 12/2002 | Weigl et al. |
| 6,531,702 | B1 | 3/2003 | Mischler et al. |
| 6,551,841 | B1 | 4/2003 | Wilding et al. |
| 6,613,512 | B1 | 9/2003 | Kopf-Sill et al. |
| 6,716,620 | B2 | 4/2004 | Bashir et al. |
| 6,818,184 | B2 | 11/2004 | Fulwyler et al. |
| 7,736,890 | B2 * | 6/2010 | Sia et al. ............... 435/287.2 |
| 8,030,057 | B2 | 10/2011 | Linder et al. |
| 2002/0019059 | A1 | 2/2002 | Chow et al. |
| 2003/0118486 | A1 | 7/2003 | Zhou et al. |
| 2003/0138969 | A1 | 7/2003 | Jakobsen et al. |
| 2003/0152927 | A1 * | 8/2003 | Jakobsen et al. ............ 435/6 |
| 2003/0175947 | A1 * | 9/2003 | Liu et al. ............... 435/288.5 |
| 2004/0077074 | A1 | 4/2004 | Ackley et al. |
| 2004/0175734 | A1 | 9/2004 | Stahler et al. |
| 2007/0298433 | A1 * | 12/2007 | Sia et al. ............... 435/7.1 |

FOREIGN PATENT DOCUMENTS

| | | |
|---|---|---|
| JP | 2002-372531 A | 12/2002 |
| JP | 2004-506189 A | 2/2004 |
| JP | 2004-98057 A | 4/2004 |
| JP | 2004-279202 A | 10/2004 |
| JP | 2005-10165 A | 1/2005 |
| JP | 2005-509158 A | 4/2005 |
| WO | WO 00/13018 A2 | 3/2000 |
| WO | WO 0013017 A | 3/2000 |
| WO | WO 02/12856 A1 | 2/2002 |
| WO | WO 03/40721 A1 | 5/2003 |
| WO | WO 03054513 A2 | 7/2003 |
| WO | WO 2004/018350 A1 | 3/2004 |

OTHER PUBLICATIONS

Office Action for Japanese Application No. 2008-507813 mailed Sep. 15, 2011.

Obeid, et al., "Microfabricated Device for DNA and RNA Amplification by Continuous-Flow Polymerase Chain Reaction and Reverse Transcription-Polymerase Chain Reaction with Cycle No. Selection," *Anal. Chem.*, vol. 75, pp. 288-295 (2003).

Sia, et al., "An Integrated Approach to a Portable and Low-Cost Immunoassay for Resource-Poor Settings," *Communications*, vol. 43, pp. 498-502 (2004).

Weigle,.et al., "Lab-on-a-chip for drug development," *Advanced Drug Delivery Reviews*, vol. 55, pp. 349-377 (2003).

International Search Report dated Nov. 8, 2006 in PCT/US2006/014583.

Office Action for Japanese Application No. 2008-507813 mailed Jun. 14, 2012.

* cited by examiner

FLUIDIC STRUCTURES INCLUDING MEANDERING AND WIDE CHANNELS

RELATED APPLICATIONS

This application is a U.S. National Application of International Application No. PCT/US06/014583, entitled "Fluidic Structures Including Meandering and Wide Channels" filed Apr. 19, 2006, which claims benefit under 35 U.S.C. §119(e) of U.S. Provisional Application Ser. No. 60/672,921, entitled "Fluidic Structures Including Meandering and Wide Channels" filed Apr. 19, 2005, each of which is hereby incorporated by reference in its entirety.

GOVERNMENT SUPPORT

This invention was made with Government support under GM065364 awarded by National Institutes of Health and under ESC-0004030 awarded by National Science Foundation. The Government has certain rights in the invention.

FIELD OF INVENTION

The present invention relates generally to microfluidic structures, and more specifically, to microfluidic structures and methods including meandering and wide channels.

BACKGROUND

Assays such as heterogeneous immunoassays (i.e., an assay where one component in the liquid phase binds with another component in the solid phase) are widely used for applications in life sciences and diagnostics, and are usually carried out in microwells. In the microwell format, however, long incubation times are typically required. As the affinity reaction proceeds, the concentration of the molecules in the layer of fluid located close to the surface decreases. Diffusion of molecules from the bulk of the solution is then needed to replenish that layer of fluid to allow more binding events to take place. Long incubation times are needed to allow the diffusion of the molecules from the bulk of the solution towards the surface. Recent developments showed that these diffusion-limited reactions take place faster in channels of micrometer dimensions, i.e. in microfluidic devices. One reason for the fast reaction times is attributed to the presence of a flow of fresh solution next to the solid phase. Incubation under flow-conditions in microchips (i.e., microfluidic chips or devices) achieves fast transport of molecules to the surface, and replenishes the layer of fluid close to the surface faster than by the diffusion mechanism.

In microfluidic channels, a small volume of solution (i.e., microliters or less) can sustain a flow sufficient for a fast replenishment of the solution close to the surface for several minutes. These features are quite attractive for the applications of immunoassays, because they result in the consumption of less solution and in faster assays compared to the microwell format. As a result, heterogeneous immunoassays in microfluidic devices have been reported frequently in the scientific literature. In these reports, the lateral dimensions of the channels were typically around 10-200 µm. These dimensions are well suited to benefit from the advantage of microfluidics for immunoassays, but they require the use of magnifying optics and the precise positioning of optics to allow detection of a signal within the channel. These techniques typically require substantial capital equipment that can be both expensive and bulky, thus limiting where and when the detection can take place. Advances in the field that could, for example, reduce costs and/or increase portability would find application in a number of different fields.

SUMMARY OF THE INVENTION

Fluidic (e.g., microfluidic) structures and methods associated therewith are provided.

In one aspect of the invention, a device is provided. The device comprises a microfluidic channel comprising a meandering region defined by an area of at least 0.5 mm$^2$, wherein at least 50% of the area of the meandering region comprises an optical detection pathway.

In another aspect of the invention, a method is provided. The method comprises exposing a meandering microfluidic channel defined by an area of at least 0.5 mm$^2$ to light, and measuring a signal over a measurement area comprising more than one adjacent segments of the meandering channel.

In another aspect of the invention, a method is provided. The device comprises a microfluidic channel comprising a meandering region, wherein at least 50% of the area of the meandering region comprises an optical detection pathway, and a detector aligned with the optical detection pathway, the detector able to detect a signal within at least 50% of the area of the meandering region.

In another aspect of the invention, a method is provided. The method comprises accumulating an opaque material on a meandering region of a microfluidic channel, exposing at least 50% of the area of the meandering region to light, and determining the transmission of light through the opaque material and through at least 50% of the area of the meandering region.

In another aspect of the invention, a method is provided. The method comprises passing a fluid over a surface of a meandering region of a microfluidic channel, allowing a sample component to bind with a binding partner disposed on the surface, allowing a metal colloid to associate with a sample component, and flowing a metal solution over the surface to form a metallic layer.

In another aspect of the invention, a method is provided. The method comprises passing a fluid over a surface of a microfluidic channel having a width of at least 1 mm, wherein the channel comprises an upper surface and a lower surface, allowing a sample component to bind with a binding partner disposed on at least one of the upper and lower surfaces, allowing a metal colloid to associate with a sample component, and flowing a metal solution over the surface to form a metallic layer.

In another aspect of the invention, a device is provided. The device comprises accumulating an opaque material on a region of a microfluidic pathway for fluid flow, wherein the pathway is defined in part by an upper surface and a lower surface, the pathway having a width, a length, and a height, at least a portion of the width being at least about 1 mm, at least a portion of the length being at least about 1 mm, and at least a portion of the height being less than or equal to about 500 µm, exposing the region to light, and determining the transmission of light through the opaque material.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention relates generally to microfluidic structures, and more specifically, to structures and methods including meandering and wide channels. Microfluidic systems can provide an advantageous environment for performing various reactions and analyses due to a reduction in sample and reagent quantities that are required, a reduction in the size of the operating system, and a decrease in reaction time compared to conventional systems. Unfortunately, the small size of microfluidic channels can sometimes result in difficulty in detecting a species without magnifying optics (such as a microscope, a photomultiplier, or an avalanche photodiode). A series of tightly packed microchannels, i.e., a meandering region, or a wide microchannel having a dimension on the order of millimeters, can serve as a solution to this problem by creating a wide measurement area. Although this invention relates to the use of meandering and wide channels in heterogeneous immunoassays on a microfluidic chip, this invention can also be used for amplifying optical signals for other types of reactions and/or assays.

Figure 1A:
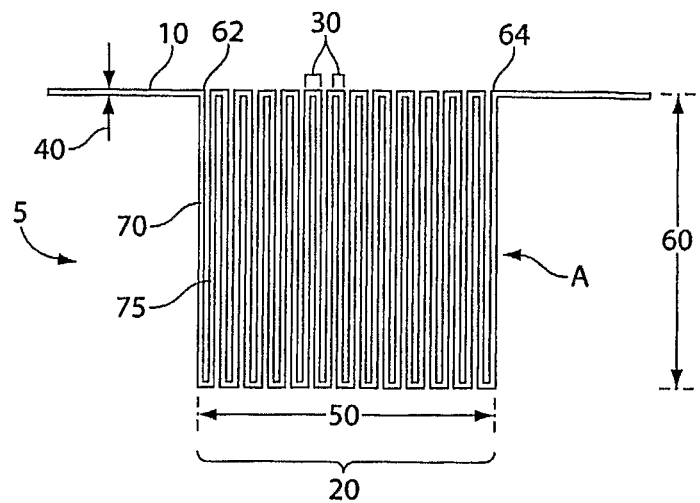
FIG. 1 shows schematically a meandering channel configuration, according to one embodiment of the invention.

FIG. 1A shows an example of a meandering channel configuration. As used herein, a meandering channel (i.e., a channel having a meandering region) includes at least a first segment that has a flow path in a first direction and a second segment that has a flow path in a second direction substantially opposite (e.g., greater than 135 degrees from) the first direction. Examples of meandering channel regions are shown in FIGS. 1 and 10. Oftentimes, a meandering channel will include more than two alternating segments that extend in opposite directions. Channel 12 includes a meandering (e.g., serpentine) region 20 that includes a tightly packed channel system having a series of turns 30 that span over a large area (A) relative to width 40 of the channel. The area spanned by the meandering channel (i.e., the area of the meandering region) is the rectangular area bound by outermost points of the meandering channel along each axis. In FIG. 1, the area (A) that meandering channel region 20 spans is defined by the surface area given by dimension 50 times (×) dimension 60. Typically, the area spanned by the channel (i.e., as viewed from above the channel, perpendicular to the direction of fluid flow) is on the order of millimeters squared ($mm^2$). For instance, the area may be greater than or equal to 0.5 $mm^2$, greater than or equal to 1 $mm^2$, greater than or equal to 2 $mm^2$, greater than or equal to 5 $mm^2$, greater than or equal to 10 $mm^2$, or greater than or equal to 50 $mm^2$. However, in other embodiments, e.g., depending on the method used for detection, the area spanned by a meandering channel may be between 0.25 $mm^2$ and 0.5 $mm^2$, or between 0.1 $mm^2$ and 0.25 $mm^2$.

Figure 1B:
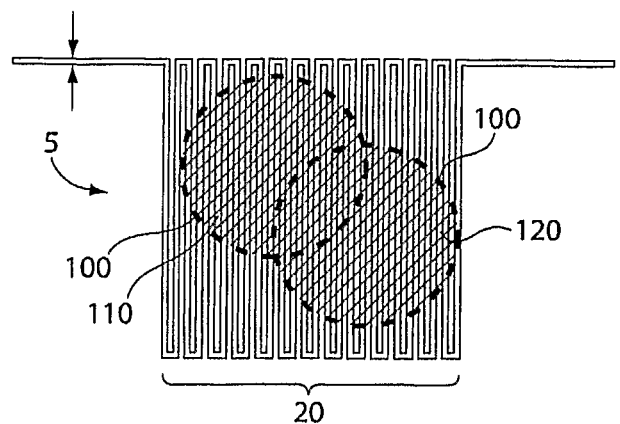

Typically, the area spanned by the meandering channel is designed to be relatively large (e.g., on the order of $mm^2$) compared to conventional microfluidic systems, so that a wide area can be used for detection and so the total amount of signal that can be detected is increased. For instance, in one embodiment, a signal detected is produced in the meandering channel, and the signal spans over the entire area (e.g., $mm^2$) of the meandering region. Thus, the detection region may span over the entire area of the meandering region. Conventional microfluidic systems, however, have a detection region on the order of square microns ($\mu m^2$), which is typically defined by the width of the microchannel. These conventional systems generally require magnifying optics such as microscopes, avalanche photodiodes, or photomultipliers, as well as precise alignment of the magnifying optics to the microchannel, in order to detect a species in the microchannel. In the meandering channel system, magnifying optics and precise alignment can be avoided since an area on the order of $mm^2$ can be detected by the naked eye. This allows a user to read a signal (e.g., a change in color, turbidity, opacity, agglutination, etc.) directly from the microchip, and/or, as shown in FIG. 1B, to align detector 100 (e.g., an optical reader) over a series of segments of the channel, rather than directly over a single microchannel. In one embodiment, detector 100 can be placed in a variety of positions by the user, e.g., positions 110 and 120, without precise alignment over region 20, since the average signal obtained from the detector in positions 110 and 120 is the same. The large area of the meandering region also allows it to be compatible with simplified optical detectors (as discussed in more detail below), as well as with conventional spectrophotometers and optical readers (e.g., 96-well plate readers).

The positioning of the detector over the meandering region without the need for precision is an advantage, since external (and possibly, expensive) equipment such as microscopes, lenses, and alignment stages are not required. Instead, alignment can be performed by eye, or by low-cost methods that may not require an alignment step by the user. In one embodiment, a microchip comprising a meandering region can be placed in a simple holder (i.e., in a cavity having the same shape as the microchip), and the measurement area can be automatically located in a beam of light of the detector. Possible causes of misalignment caused by, for instance, chip-to-chip variations, the exact location of the chip in the holder, and normal usage of the device, are negligible compared to the dimensions of the measurement area. As a result, the meandering region can stay within the beam of light and detection may not be interrupted due to these variations.

Detector 100 may be aligned over meandering channel region 20 to varying degrees and may depend on, for instance, the number of detectors aligned over the region, the size of the detector, and/or the size of the area of the meandering region. In one embodiment, the detector can align within at least 25% of area of the meandering region. In another embodiment, the detector can align within at least 50% of area of the meandering region. In yet another embodiment, the detector can align within at least 75% of area of the meandering region. A small area covered by the detector (e.g., 25% or less of the area of the meandering region) may be suitable for aligning several detectors over the region (e.g., for determining different signals within different portions of the channel within the region). A large area covered by the detector (e.g., 75% or more of the area of the meandering region) may occur when aligning a single detector over the region (e.g., if the detector and the region are of similar size).

The detector may detect a signal within all, or a portion, of the meandering region. In other words, different amounts of the meandering region may be used as an optical detection pathway. For instance, the detector may detect a signal within at least 25% of the meandering region, within at least 50% of the meandering region, or within at least 75% of the meandering region. In some instances, 100% of the meandering region is used for detection by a detector (e.g., detection in a transparent channel by the unaided eye). The area in which the meandering region is used as an optical detection pathway may also depend on, for instance, the opacity of the material in which the channel is fabricated (e.g., whether all, or, a portion, of the channel is transparent), the amount of a non-transparent material that may cover a portion of the channel (e.g., via use of a protective cover), and/or the size of the detector and the meandering region.

The spacing of adjacent channel segments 70 and 75 (FIG. 1A) of the meandering channel can vary depending on the application. In some embodiments, segments 70 and 75 are separated by a distance of less than 1 mm, less than 500 µm, less than 250 µm, less than 100 µm, less than 50 µm, less than 25 µm, less than 10 µm, less than 5 µm, less than 1 µm, or less than 0.1 µm. For example, segments 70 and 75 may be separated by a distance of less than 0.01 times, less than 0.1 times, less than 0.25 times, less than 0.5 times, less than 1 times, less than 2 times, less than 5 times, or less than 10 times channel width 40. In some particular embodiments, observable gaps may not exist between segments, e.g., two adjacent segments may appear as a single segment. In some instances, it may be desirable to place adjacent segments close together (e.g., separated by less than 0.25 times channel width 40) so that more of a signal can be generated over a given area (i.e., less area is covered by non-channel regions). In other cases, adjacent segments may be placed farther apart (e.g., separated by greater than 5 times channel width 30). This can be useful, for example, if the concentration of detectable species in the channel is high, if the detectable signal gives a binary (e.g., yes/no) response, and/or if it is desirable to have a channel having a relatively short length.

As shown in FIG. 1, the length of segments 70 and 75 are the same. In other embodiments, however, the lengths of the segments of the meandering channel vary within the channel. For instance, as shown in FIG. 2, segments 80 and 85 have different lengths, since meandering channel 15 has a circular shape. The meandering channel (and the area of the channel) can be designed to have any shape, e.g., a square, rectangular, circular, oval, triangular, spiral, or an irregular shape, since the overall shape does not affect the fluid flow conditions within the channel, as discussed in more detail below.

The meandering channels are not limited by the number and/or the degree of turns that make up the channel. For instance, in FIG. 1 turn 30 is a 180 degree turn, and meandering channel region 20 is made up of 25 of these turns. In FIG. 2, turn 35 is also a 180 degree turn, and meandering channel 15 is made up of 34 of turns 35. Meandering channels having areas of different shapes, e.g., a spiral shape, and other configurations are also possible (FIG. 10).

The meandering channel has at least one cross-sectional dimension in the micron range so that it can retain its advantageous qualities of micro-scale geometry (e.g., laminar flow, fast reaction times, small volumes, etc.). For example, the cross-sectional dimension may be less than 1 mm, less than 500 µm, less than 250 µm, less than 100 µm, less than 50 µm, or less than 25 µm. In some instances, it is desirable to have a channel having a relatively large cross-sectional dimension (e.g., a height of 500 µm), for example, to increase the path length of the channel; this configuration may be useful for detecting a weak signal that depends on the amount of detectable species solvated or suspended in the fluid (e.g., colorimetric detection), rather than the amount of detectable species formed on the surface of the channel. In some cases, a channel may be designed to have a width greater than about 75 µm, so that gas bubbles can pass easily through the channel, as described below. In other cases, a small cross-sectional dimension (e.g., 50 µm or less) is suitable, e.g., for flowing very small amounts of fluid in the device. A cross-sectional dimension in the micron range also allows transport of fresh solution over the surface of the channel without the use of large amounts of fluid.

Different types of binding, including those that involve chemical and/or biological reactions, may take place in a meandering channel. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

In some cases, a heterogeneous reaction (or assay) may take place in the channel; for example, a binding partner may be associated with a surface of a channel, and the complementary binding partner may be present in the fluid phase. The term "binding partner" refers to a molecule that can undergo binding with a particular molecule. Biological binding partners are examples; for instance, Protein A is a binding partner of the biological molecule IgG, and vice versa. Likewise, an antibody is a binding partner to its antigen, and vice versa. In other cases, a homogeneous reaction may occur in the channel. For instance, both binding partners can be present in the fluid phase (e.g., in two-fluid laminar flow system). Non-limiting examples of typical reactions that can be performed in a meandering channel system include chemical reactions, enzymatic reactions, immuno-based reactions (e.g., antigen-antibody), and cell-based reactions.

In one embodiment, a signal produced by the reaction is homogenous over the entire meandering region. In other words, a signal produced in a first segment of the meandering channel is similar to a signal produced in a second, adjacent segment of the channel, which is similar to the signal produced in all additional segments of the meandering channel (e.g., all 26 segments of FIG. 1). Such a signal can enable a detector to be positioned over any portion of the meandering region and allow similar signals to be detected by the detector, as shown earlier in FIG. 1B and as described in Example 4. In another embodiment, the signal may be homogeneous over only portions of the meandering region, and one or more detectors may detect different signals within each of the portions. For instance, a signal produced in a first segment of the meandering channel may be similar to a signal produced in a second, adjacent segment of the channel, but this signal may be different from the signal produced in, e.g., the $7^{th}$ and $8^{th}$, segments of the meandering channel. In yet another embodiment, the signal may generate a gradient over the meandering region, e.g., such that the extent of the reaction varies depending on the location within the channel (e.g., the signal is different in each segment of the channel).

Figure 8:
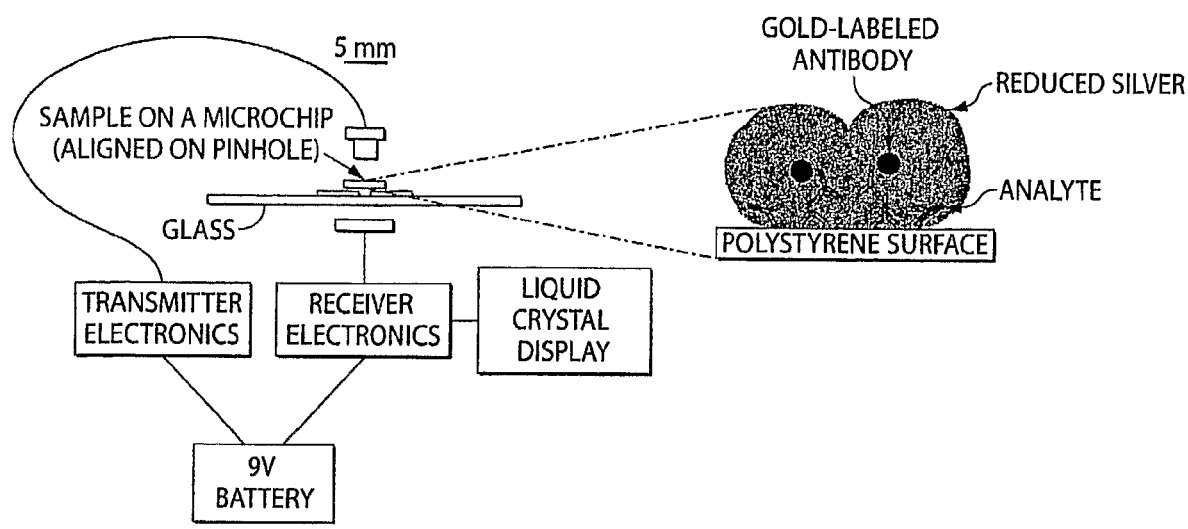
FIG. 8 shows schematically an example of a detection device and method, according to another embodiment of the invention.

In some embodiments, a meandering channel may be used in combination with an amplification system that increases the amount of signal formed in the channel, such as amplification by silver enhancement. Additionally and/or alternatively, precipitating dyes or other materials (e.g., fluorescent molecules or chemiluminescent species) that can form an optically-detectable layer can be used in combination with a meandering channel. For instance, a sample can be flowed over a surface associated with a prospective binding partner of a sample component. The assay can be performed in a meandering channel of a microfluidic device allowing the sample to be flowed over a binding partner, for example, an antigen. Any antigen-antibody complex that forms may be associated with a metal colloid (e.g., a gold colloid) that provides a catalytic surface for the deposition of an opaque material, such as a layer of metal (e.g., silver), on a surface of the channel. Therefore, if antibody-antigen binding occurs in the microfluidic channel, the flowing of a metal precursor through the channel can result in the formation of an opaque layer (i.e., a substance that interferes with the transmittance of light at one or more wavelengths), such as a silver layer, due to the presence of the catalytic metal colloid associated with the antibody-antigen complex (FIG. 8). Any opaque layer that is formed in the microfluidic channel can be detected optically, for example, by measuring a reduction in light transmittance through a portion of the microfluidic channel compared to a portion of the channel that does not include the antibody or antigen. The opaque layer may provide an increase in assay sensitivity when compared to techniques that do not form an opaque layer. Examples of this amplification system are described in Examples 2 and 3, and in further detail in International Patent application Serial No.: PCT/US04/043585 by Sia et al., filed Dec. 29, 2004, which is incorporated herein by reference, which is herein incorporated by reference.

Figure 2A:
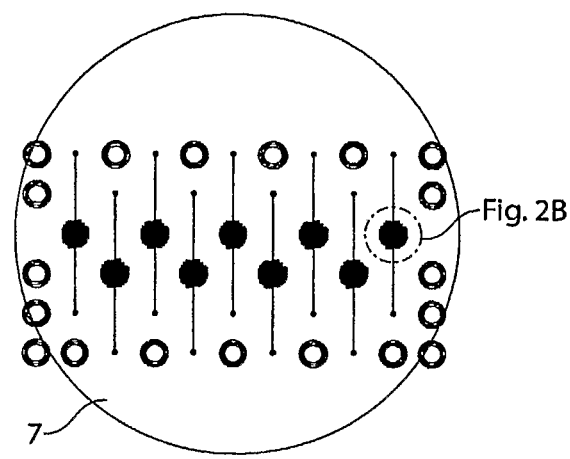
FIG. 2 shows schematically another meandering channel configuration, according to another embodiment of the invention.
Figure 3A:
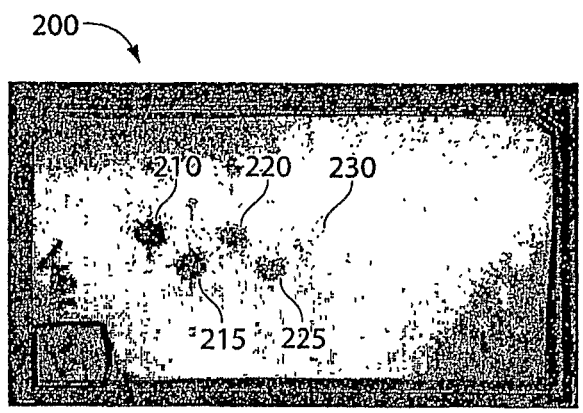
FIG. 3 shows photographs of the results of immunoassays performed in a meandering channel configuration, according to another embodiment of the invention.

FIG. 3 shows the results of heterogeneous immunoassays that were performed using a device (similar to microchip 7 in FIG. 2A) that included several meandering regions (see Examples 2 and 3 for more details). In FIG. 3A, substrate 200 (the bottom portion of the device) contains five reaction regions, 210, 215, 220, 225, and 230, in the shape of the meandering channels of the device. As expected, regions having higher concentrations of reactant gave larger signals (e.g., region 210) compared to regions containing lower concentrations of reactant (e.g., region 230). These results are summarized in FIGS. 4 and 5 for reactions on substrates 201 and 202, respectively.

In some cases, a microchip having meandering regions may be used in combination with off-chip instrumentation (e.g., a detector). The meandering regions can be shaped and configured to fit the geometry of a specific instrument, such as a 96-well plate reader. FIG. 3A shows several regions (210, 215, 220, 225, and 230) that are spaced apart according to the spacing of the wells in a 96-well plate. This configuration allows the meandering regions to be used in combination with a 96-well reader, which can optically detect several reactions (i.e., in regions 210, 215, 220, 225, and 230) on the microchip simultaneously.

Figure 9:
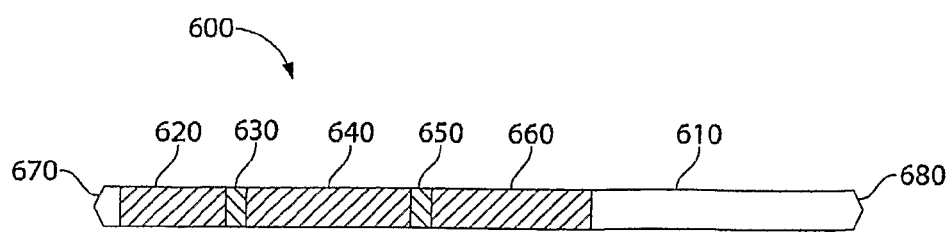
FIG. 9 shows a vessel used for delivering fluids into a microfluidic device, according to another embodiment of the invention.
Figure 10A:
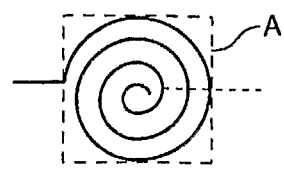
FIG. 10 shows schematically examples of different shapes and configurations of meandering channels, according to another embodiment of the invention.
Figure 10B:
Figure 10C:
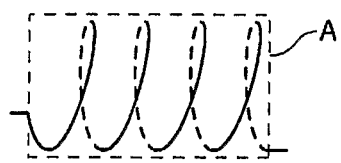
Figure 10D:
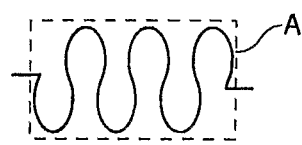
Figure 10E:
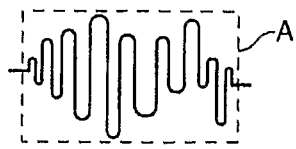

Fluids may be introduced into meandering channels using any suitable method, such as by pipet, syringe, syringe pump, vacuum, or fluid cartridge. In one embodiment, a vessel containing two or more distinct fluids, separated by a third fluid that is immiscible with both, is used to introduce fluids into a meandering channel. As illustrated in FIG. 9, vessel 600 may be a tube 610 having a longitudinal cross-section that includes a reagent solution plug 620, followed by an air plug 630, followed by a rinse solution plug 640. An additional air plug 650 may separate the first rinse solution plug from second rinse solution plug 660. The ends of the tube 670 and 680 may be sealed, for example, to retain the plugs and to prevent contamination from external sources. The liquid plugs may retain their relative positions in the tube and may be prevented from contacting each other by the interspaced air plugs. The tube dimensions and materials of construction may be chosen to help fluid plugs retain their position and remain unmixed. The vessel is described in more detail in International Patent application Serial No.: PCT/US 05/03514 by Linder et al., filed Jan. 26, 2005, which is incorporated herein by reference.

Reagents and other fluids may be stored for extended lengths of time in the vessel. For example, reagents may be stored for greater than 1 day, 1 week, 1 month or 1 year. By preventing contact between fluids, fluids containing components that would typically react or bind with each other are prevented from doing so, while being maintained in a continuous chamber.

Fluids may be transferred from the vessel to be used in a process, for example, to participate in a reaction or assay. Fluids may be transferred from the vessel by applying pressure or vacuum after removing or piercing the seal at ends 670 and 680. In other embodiments, the vessel need not be sealed and fluid flow can be started by applying an external force, such as a pressure differential. One end of the vessel, for example, end 670, can be in or can be placed in fluid communication with another device that will receive the fluids from the vessel. Such a device may include, for example, a reaction site of a reactor or an assay, which can including a meandering channel region.

A vessel containing fluid plugs may be put in fluid communication with a reaction site and fluids may be flowed from the vessel to the reaction site. For instance, the fluids may be flowed to a microfluidic immunoassay, some embodiments of which are described herein. The vessel containing the fluid plugs may be separate from a device including the reaction site or may be part of the same platform. Fluid may be flowed to the reaction site by, for example pushing or pulling the fluid through the vessel. Fluids can be pushed to the reaction site using, for example, a pump, syringe, pressurized vessel, or any other source of pressure. Alternatively, fluids can be pulled to the reaction site by application of vacuum or reduced pressure on a downstream side of the reaction site. Vacuum may be provided by any source capable of providing a lower pressure condition than exists upstream of the reaction site. Such sources may include vacuum pumps, venturis, syringes and evacuated containers.

In one set of embodiments, a vessel may contain fluid plugs in linear order so that as fluids flow from the vessel to a reaction site they are delivered in a predetermined sequence. For example, an assay may receive, in series, an antibody fluid, a rinse fluid, a labeled-antibody fluid and a rinse fluid. By maintaining an immiscible fluid (a separation fluid) between each of these assay fluids, the assay fluids can be delivered in sequence from a single vessel while avoiding contact between any of the assay fluids. Any immiscible fluid that is separating assay fluids may be applied to the reaction site without altering the conditions of the reaction site. For instance, if antibody-antigen binding has occurred at a reaction site, air can be applied to the site with minimal or no effect on any binding that has occurred.

In one embodiment, at least two fluids may be flowed in series from a common vessel, and a component of each fluid may participate in a common reaction. As used herein, "common reaction" means that at least one component from each fluid reacts with the other after the fluids have been delivered from the vessel, or at least one component from each fluid reacts with a common component and/or at a common reaction site after being delivered from the vessel. For example, a component of the first fluid may react with a chemical or biological entity that is downstream of the vessel. A chemical or biological entity may form a reaction site and may be, for example, a sample, a biological or chemical compound, a cell, a portion of a cell, a surface or a substrate. The chemical or biological entity may be fixed in position or may be mobile. A component from the second fluid may then react and/or associate with the component from the first fluid that has reacted with the downstream chemical or biological entity, or it may react or associate with the chemical or biological entity itself. Additional fluids may then be applied, in series, to the biological or chemical entity to effect additional reactions or binding events or as indicators or signal enhancers.

Pre-filling of the vessel with reagents may allow the reagents to be dispensed in a predetermined order for a downstream process. In cases where a predetermined time of exposure to a reagent is desired, the amount of each fluid in the vessel may be proportional to the amount of time the reagent is exposed to a downstream reaction site. For example, if the desired exposure time for a first reagent is twice the desired exposure time for a second reagent, the volume of the first reagent in the vessel may be twice the volume of the second reagent in the vessel. If a constant pressure differential is applied in flowing the reagents from the vessel to the reaction site, and if the viscosity of the fluids is the same or similar, the exposure time of each fluid at a specific point, such as a reaction site, may be proportional to the relative volume of the fluid. Factors such as vessel geometry, pressure or viscosity can also be altered to change flow rates of specific fluids from the vessel.

When designing a microfluidic device for use with a particular component, e.g., a fluid vessel as described above, certain aspects of the design may have to be taken into consideration. For instance, the dimensions of the meandering channel (e.g., channel size and aspect ratio of the channel) may be chosen to avoid the retention of air bubbles within the device, since air bubbles can cause inaccurate detection of a signal. This can configuration may allow multiple meandering regions to be positioned in series. Generally, channels with larger cross-sectional dimensions avoid the trapping of air bubbles more than channels with smaller cross-sectional dimensions, since large dimensions allow the bubbles to have less surface area in contact with the walls of the channel. Channels having a width of greater than 25 µm, greater than 50 µm, greater than 75 µm, greater than 100 µm, or greater than 200 µm may be suitable for avoiding the trapping of air bubbles, depending aspects such as the size/volume of the air pockets introduced into the device, the fluids surrounding the air bubbles, and the hydrophilicity/hydrophobicity of the walls of the channel.

In another embodiment, a wide channel or a chamber having a surface area on the order of millimeters squared ($mm^2$) is used a reaction site on a microfluidic chip. For instance, the width of the channel or chamber may be greater than or equal to 0.5 mm, greater than or equal to 1 mm, greater than or equal to 2 mm, greater than or equal to 5 mm, greater than or equal to 10 mm. The area covered by the wide channel is designed to be relatively large (e.g., on the order of $mm^2$) compared to conventional microfluidic systems, so that a wide area can be used for detection and so the total amount of signal that can be detected is increased. For instance, the surface area covered by the wide channel may be greater than or equal to 0.5 $mm^2$, greater than or equal to 1 $mm^2$, greater than or equal to 2 $mm^2$, greater than or equal to 5 $mm^2$, greater than or equal to 10 $mm^2$, or greater than or equal to 50 $mm^2$. As shown in FIG. 7, fluidic chip 400 comprises several wide channels 410. The area that wide channel 410 covers is defined by the square area given by dimension 420 times (×) dimension 430.

Similar to a meandering channel, a wide channel or chamber having dimensions on the order of square-millimeters allows a user to read a signal (e.g., a change in color, turbidity, opacity, agglutination, etc.) directly from the microchip, and/or, to align a detector over a wide portion of the channel, rather than over a narrow (e.g., µm) portion of the channel, as is typical in conventional microfluidic systems. The large area of wide channel 410 also allows it to be compatible with simplified optical detectors (as discussed below), as well as with conventional spectrophotometers and optical readers (e.g., 96-well plate readers).

Wide channel 410 has an upper surface, a lower surface, and may optionally comprise posts (e.g., posts 440, 450, and/or 460) disposed between the upper and lower surfaces. As shown in FIG. 7, posts 440, 450, and/or 460 may have different shapes and/or configurations. In some cases, the posts are used to give support to the upper and lower surfaces. For instance, wide channels fabricated in an elastomer may require posts to prevent the upper surface and lower surface from contacting each other. Posts can also be used in microfluidic systems for other purposes such as for mixing and filtering.

Wide channel 410 has at least one cross-sectional dimension in the micron range so that it can retain its advantageous qualities of micro-scale geometry (e.g., laminar flow, fast reaction times, small volumes, etc.). For example, the cross-sectional dimension may be less than 1 mm, less than 500 µm, less than 250 µm, less than 100 µm, less than 50 µm, or less than 25 µm. A cross-sectional dimension in the micron range also allows transport of fresh solution over the surface of the channel without the use of large amounts of fluid.

In some cases, it is advantageous to use a wide channel region over a meandering channel region, e.g., for performing a reaction or assay. For instance, when mixing is desired, e.g., mixing two or more solutions or two or more components within a solution, it may be suitable to use a wide channel region (with or without posts). In other cases, it is advantageous to use a meandering channel region over a wide channel region. For example, if mixing is not desired, or if gas bubbles are introduced into the fluidic system, meandering channels may be more suitable. In some instances, a microfluidic device comprises both a wide channel region and a meandering region, e.g., when mixing is desired in one portion of the device but not desired in another.

A variety of determination techniques may be used. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred.

In some embodiments, determination techniques may measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver nitrate solution is used, a silver sensitive electrode may be capable of measuring a loss in silver concentration due to the deposition of silver in a channel as the precursor passes through the channel.

Different optical detection techniques provide a number of options for determining assay results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. The system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

In one embodiment, the light source can be pulse modulated, for example, at a frequency of 1,000 Hz. To match the pulse modulated light source, a detector may include a filter operating at the same frequency. By using a pulse modulated light source it has been found that the system can be less sensitive to extrinsic sources of light. Therefore, the assay may run under various light conditions, including broad daylight, that might make it impractical to use existing techniques. Experimental results indicate that by using a pulse modulated light source and filter, results are consistent regardless of the light conditions under which the test is run.

The light source may be a laser diode. For example, an InGaAlP red semiconductor laser diode emitting at 654 nm may be used. The photodetector may be any device capable of detecting the transmission of light that is emitted by the light source. One type of photodetector is an optical integrated circuit (IC) including a photodiode having a peak sensitivity at 700 nm, an amplifier and a voltage regulator. If the light source is pulse modulated, the photodetector may include a filter to remove the effect of light that is not at the selected frequency.

Though in some embodiments, systems of the invention may be microfluidic, in certain embodiments, the invention in not limited to microfluidic systems and may relate to other types of fluidic systems. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

A microfluidic device of the invention can be fabricated of any material suitable for forming a microchannel. Non-limiting examples of materials include polymers (e.g., polystyrene, polycarbonate, poly(dimethylsiloxane), and a cyclo-olefin copolymer (COC)), glass, and silicon. Those of ordinary skill in the art can readily select a suitable material based upon e.g., its rigidity, its inertness to (i.e., freedom from degradation by) a fluid to be passed through it, its robustness at a temperature at which a particular device is to be used, and/or its transparency/opacity to light (i.e., in the ultraviolet and visible regions).

In some instances, the body is comprised of a combination of two or more materials, such as the ones listed above. For instance, the channels of the device may be formed in a first material (e.g., poly(dimethylsiloxane)), and a substrate that is formed in a second material (e.g., polystyrene) may be used as the base to seal the channels.

In some cases, the device is fabricated using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, for example, a glass slide, silicon wafer, or polystyrene surface may be placed against the PDMS surface and may be held in place by van der Waals forces, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

The following examples are intended to illustrate certain embodiments of the present invention, but are not to be construed as limiting and do not exemplify the full scope of the invention.

Example 1

Fabrication and Design of a Meandering Channel System

A method for fabricating and designing a meandering channel system is described. Using rapid prototyping techniques, a master of SU8-50 photoresist was produced on a silicon wafer. The master was used to replicate the negative pattern in PDMS. The height of the photoresist features was 52 µm. The master was silanized with (tridecafluoro-1,1,2,2-tetrahydrooctyl)trichlorosilane (ABC-R, Germany). PDMS (Silgard 184, Dow Corning, from Distrelec, Nänikon, Switzerland) was mixed according to the manufacturer's instructions and poured onto the master. After polymerization (4 hours, 65°), the PDMS replica was peeled off the master and access holes were punched out of the PDMS using brass tubing with sharpened edges (1.5 mm in diameter).

Figure 2B:
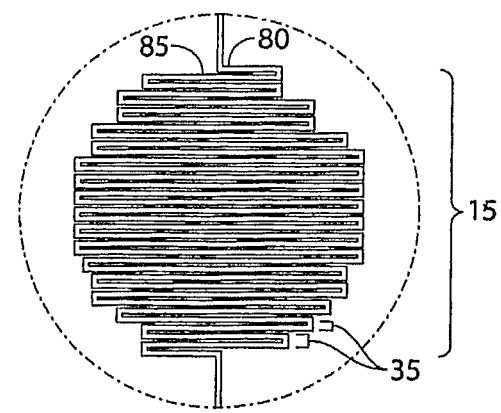

The layout of the channel system was designed with a computer-aided design (CAD) program and is illustrated in FIG. 2A. The channels were 120 µm in width, and the area of the meandering region covered the surface of a well in a 96-well plate. The positions of the meandering regions relative to one other were the same as that of wells in a 96-well plate. This arrangement enabled the PDMS replica to be placed onto a "NUNC plate", a plate having the same dimensions as the 96-well plate but without the wells. This arrangement was chosen so that the quantification of the signal generated inside the meandering region could be performed with a standard ELISA plate reader, as well as with other types of optical detectors.

Example 2

Immunoassay Experiment Using Silver Enhancement

An immunoassay experiment was performed using the meandering channel system as described in Example 1. In preparation for the assay, the surface of a NUNC plate was spotted with an array of droplets of human IgG (50 µg/mL in PBS). Each droplet covered a circle of ~1 cm in diameter, each droplet being aligned with the location of a microfluidic meandering region (based on a 96-well plate as the template). The protein solution was left to incubate overnight at 4° C. The plates were rinsed with deionized water, dried with a stream of nitrogen, and the PDMS replica was sealed (conformally, i.e., without plasma oxidation) to the NUNC plate. A 96-well plate was used as a template to align the meandering regions to the spots of human IgG on the NUNC plate. The microchannels were filled with a solution of 0.05% Tween in phosphate-buffered saline (PBS), which allowed blocking of the surface of the microchannels for 1 hour at 4° C.

An immunoassay was performed using fluid vessels (in the form of a tube), as described previously. The buffer used for the assay was 0.05% Tween in PBS. Sections of PE60 tubing were prepared, and filled with a succession of reagents, each reagent being separated by pockets of air (e.g., air bubbles). The section of tubing was filled with 5 cm (23 µL) of labeled anti-human IgG (labeled with either gold colloids, or with horseradish peroxidase (Example 3)), prepared at various concentrations by serial dilution with buffer, followed by three 3-mm long plugs of buffer, and a 10-mm long plug of buffer. The tubing was fitted into an inlet of the microchip, the inlet in fluid communication with the meandering channels. A negative pressure (−15 kPa) applied at the outlet of the channel drew all of the reagents from the cartridge and though the meandering regions of the microchip. When all of the reagents had passed through the meandering regions, the empty cartridge was disconnected from the microchip and an amplification solution was pipetted into the inlet of the channel while the negative pressure was maintained.

Figure 3B:
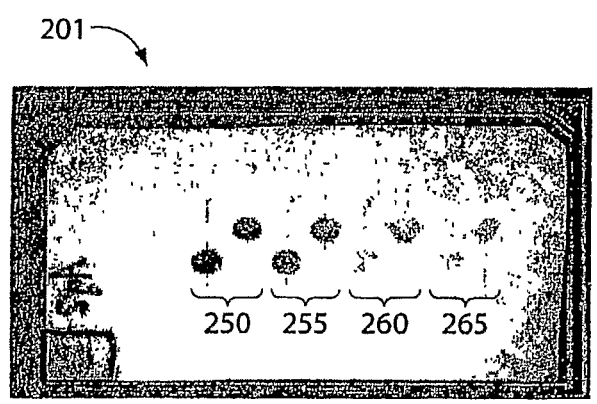

For amplification targeting anti-human IgG labeled with gold colloids (Sigma, St-Louis), a solution for electroless silver deposition (Sigma) was used as the amplification solution. The solution was freshly prepared from the two components (silver nitrate and hydroquinone), mixed in equal amounts. The silver solution remaining at the inlet was exchanged with another freshly prepared solution every 6 minutes. Amplification was continued until a clear signal was observable by the naked eye (18 minutes), as shown in FIGS. 3A and 3B. Channels containing higher concentrations of reagent (gold-labeled anti-human IgG) gave larger signals. In FIG. 3A, the dilution of gold-labeled anti-human IgG was 1:50 (region 210), 1:500 (region 215), 1:1500 (region 220), 1:5000 (region 225), and 1:50,000 (region 23). In FIG. 3B, the dilution of gold-labeled anti-human IgG was 1:50 (region 250), 1:500 (region 255), 1:5000 (region 260), and 1:50,000 (region 265).

Figure 4:
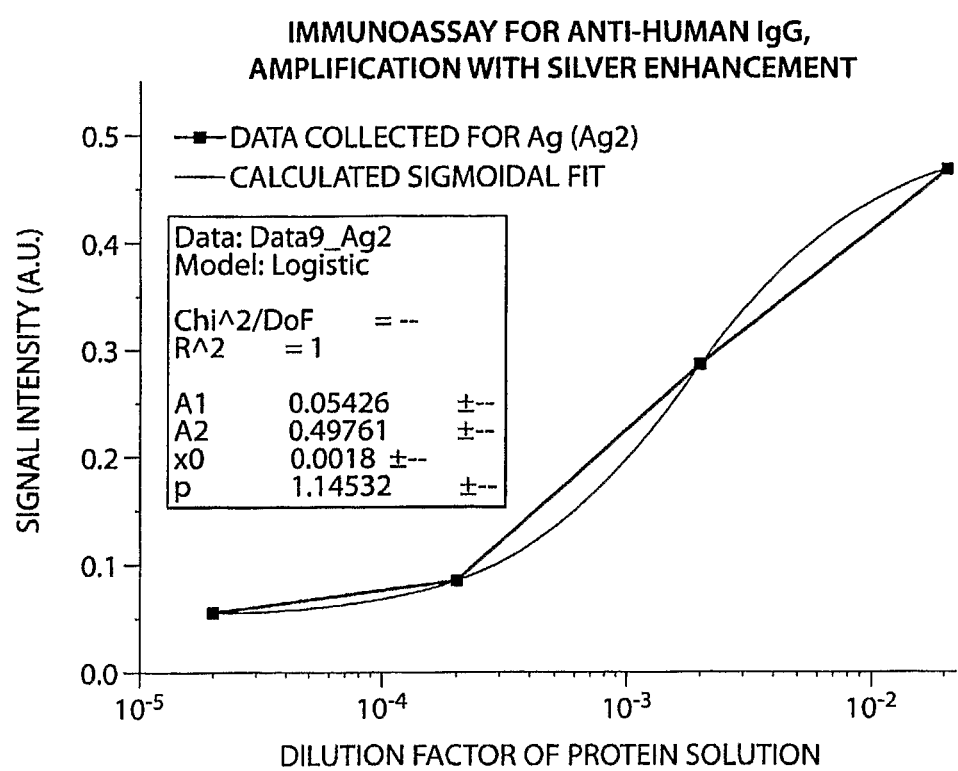
FIG. 4 shows graphically the results of an immunoassay based on amplification by silver enhancement, according to another embodiment of the invention.

The channels were rinsed with PBS, and the PDMS structure containing the meandering channels was removed the from the NUNC plate. The surface of the PDMS was dried using a stream of nitrogen. Optical density measurements (of several reactions, obtained simultaneously) with an ELISA reader showed results that were consistent with the intensities visible by eye. A sigmoidal calibration curve was obtained for all substrates. FIG. 4 shows a calibration curve obtained for the anti-human IgG assay with amplification by silver enhancement, based on the experiment shown in FIG. 3B.

Example 3

Immunoassay Experiment Using Enzymatic Amplification and Precipitating Dyes

An immunoassay experiment was performed using the meandering channel system of Example 1, and following similar procedures as described in Example 2, but with enzymatic amplification and the precipitating dye DAB instead of silver enhancement.

Figure 3C:
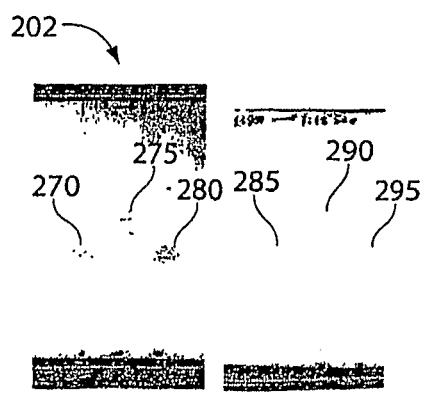

For amplification with horseradish peroxidase labeled anti-human IgG (Sigma), a freshly-prepared solution of DAB (diaminobenzidine) (Fluka, Switzerland) was used. DAB was dissolved in DMSO at a concentration of 10 mg/mL to obtain a stock solution of DAB. The working solution was prepared by diluting 100-fold the stock solution of DAB in PBS, and by adding hydrogen peroxide (30%, Rockwood, France) to obtain a final dilution of 1:3000 in hydrogen peroxide. The amplification solution was drawn into the meandering region until a signal was visible by eye (i.e., 30 minutes), as shown in FIG. 3C. In FIG. 3C, the dilution of labeled anti-human IgG was 1:10 (region 270), 1:50 (region 275), 1:100 (region 280), 1:500 (region 285), 1:2,500 (region 290), and 1:12,500 (region 295).

Figure 5:
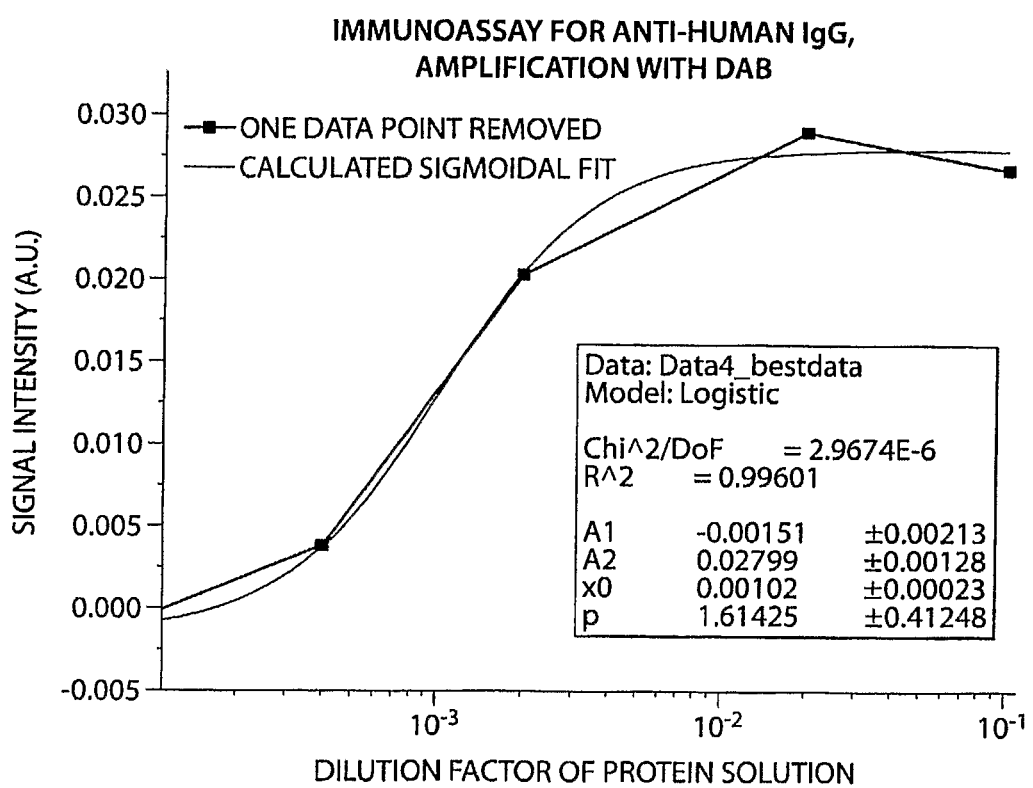
FIG. 5 shows graphically the results of an immunoassay based on amplification by a precipitating dye, according to another embodiment of the invention.

FIG. 5 shows the result of the assay shown in FIG. 3C, using an ELISA plate reader as the detector. Although the amplification was carried out for 30 minutes (compared to 18 minutes for the silver enhancement amplification), the intensities were much smaller using DAB amplification than those obtained with the silver chemistry. Under conditions for DAB amplification, the linear range of the calibration curve was close to 1000-fold dilution of anti-human IgG. Both silver and DAB amplification chemistries could thus be used for the quantification of heterogeneous assays.

Example 4

Alignment of the Meandering Channels

Figure 6:
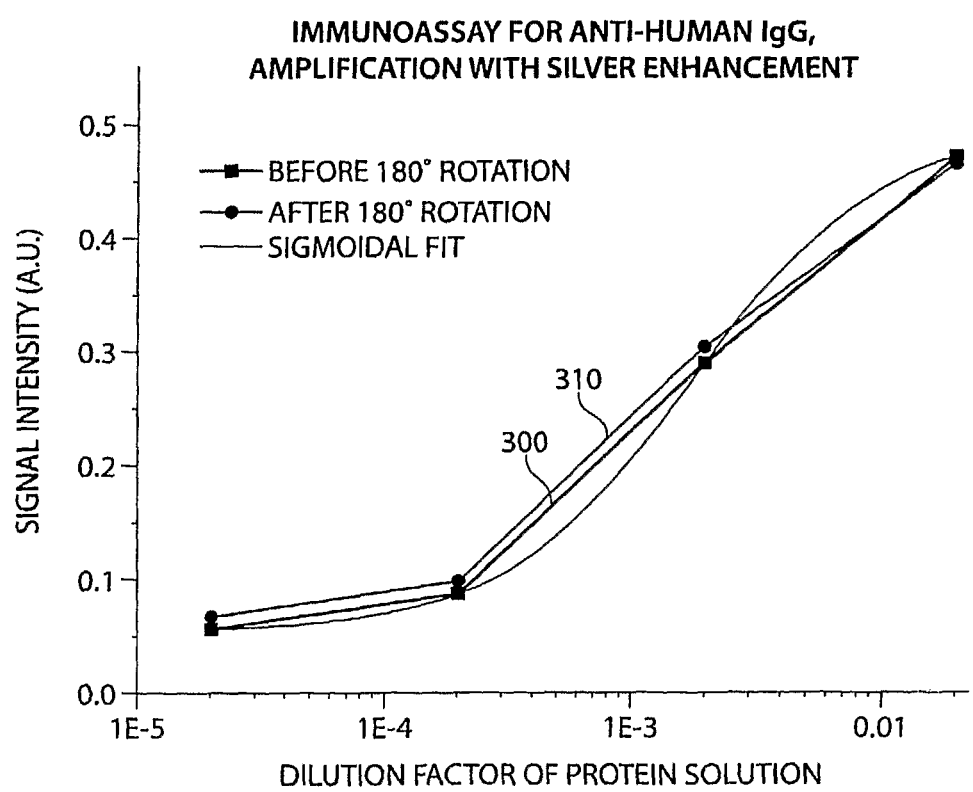
FIG. 6 shows graphically the result of an immunoassay before and after the substrate is rotated relative to a detector, according to another embodiment of the invention.
Figure 7A:
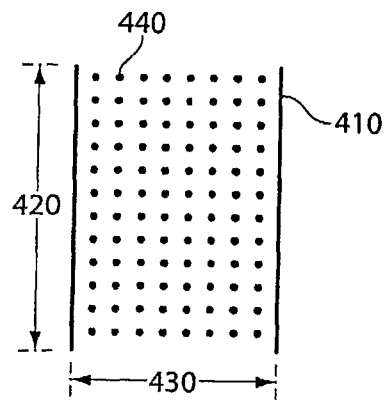
FIG. 7 shows a wide channel configuration, according to another embodiment of the invention.
Figure 7B:
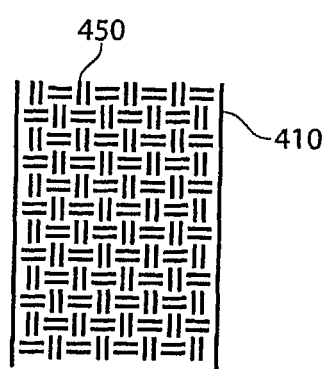
Figure 7C:
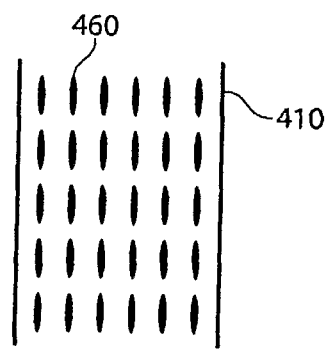
Figure 7D:
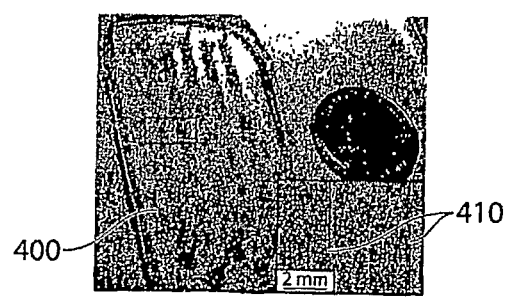

The data in FIG. 6 were obtained with only mm-range precision of alignment between the meandering regions and the light beam of the detector (in this example, an ELISA reader). Curves 300 and 310 show that after rotating the substrate 180 degrees (around the z-axis) relative to the ELISA reader, similar signals were detected. Both sets of results were within the expected results for the assay. These results indicate that the width of the light beam of the ELISA reader was sufficiently larger than the width of the microchannel, and encompassed several segments of the meandering channel. In this configuration, only the alignment of the light beam to the mm-sized meandering region was necessary, instead of careful alignment to an individual section of the meandering region. The signal detected from each of the meandering regions remained unchanged, despite the loss of initial alignment between the microchannels and the beam of light.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
   carrying out a chemical and/or biological reaction in a meandering region of a microfluidic channel;
   exposing the meandering region to light, wherein the meandering region has an area of at least 0.5 mm$^2$; and
   measuring a signal averaged over more than one adjacent segments of the microfluidic channel in the meandering region.

2. A method as in claim 1, wherein the signal is a light transmittance signal.

3. A method as in claim 1, wherein determining the signal comprises using an optical system that does not comprise an optical magnifying component.

4. A method as in claim 1, wherein a first portion of the signal, measured from a first segment of the microfluidic channel in the meandering region, is substantially the same as a second portion of the signal, measured from a second, adjacent segment of the microfluidic channel in the meandering region.

5. A method as in claim 1, wherein a portion of the signal, measured from a first segment of the microfluidic channel in the meandering region, is substantially the same as a portion of the signal measured from at least 5 adjacent segments of the microfluidic channel in the meandering region.

6. A method as in claim 1, wherein the meandering region has an area of at least 2 mm$^2$.

7. A method as in claim 1, wherein the meandering region has an area of at least 4 mm$^2$.

8. A method comprising:
   passing a fluid over a surface of a meandering region of a microfluidic channel, wherein at least a portion of the microfluidic channel in the meandering region has a width of less than 0.5 mm;
   allowing a sample component to bind with a binding partner disposed on the surface;
   allowing a metal colloid to associate with a sample component;
   flowing a metal solution over the surface to form a metallic layer; and
   measuring a signal averaged over more than one adjacent segments of the microfluidic channel in the meandering region.

9. A method as in claim 8, wherein the signal is a transmittance signal.

10. A method as in claim 8, wherein the signal is measured without using magnifying optics.

11. A method as in claim 8, wherein the metal colloid comprises gold.

12. A method as in claim 8, wherein the metal colloid comprises a gold-conjugated antibody.

13. A method as in claim 8, wherein the metal solution comprises silver.

14. A method as in claim 8, further comprising measuring conductivity of the metallic layer.

15. A method comprising:
   passing a fluid over a surface of a meandering region of a microfluidic channel, wherein at least a portion of the microfluidic channel in the meandering region has a width of less than 0.5 mm, and wherein the microfluidic channel comprises an upper surface and a lower surface;
   allowing a sample component to bind with a binding partner disposed on at least one of the upper and lower surfaces;
   allowing a metal colloid to associate with a sample component;
   flowing a metal solution over the surface to form a metallic layer; and
   measuring a signal averaged over more than one adjacent segments of the microfluidic channel in the meandering-region.

16. A method of claim 15, wherein at least a portion of the microfluidic channel in the meandering region has a width of less than 250 microns.

17. A method as in claim 1, wherein the microfluidic channel in the meandering region comprises a binding partner adsorbed to a surface of the microfluidic channel.

18. A method as in claim 17, wherein the binding partner comprises an antibody or an antigen.

19. A method as in claim 1, wherein the chemical and/or biological reaction is a binding event between at least two binding partners, and wherein at least one of the binding partners comprises an antibody.

20. A method as in claim 1, wherein at least a portion of the microfluidic channel in the meandering region has a width of less than 500 microns.

21. A method as in claim 1, wherein at least a portion of the microfluidic channel in the meandering region has a width of less than 250 microns.

22. A method as in claim 1, comprising forming an opaque material in the meandering region of the microfluidic channel, and quantitatively determining the opacity of the opaque material.

23. A method as in claim 22, wherein quantitatively determining the opacity of the opaque material comprises measuring transmission of light through the opaque material through at least 25% of the area of the meandering region.

24. A method as in claim 1, wherein the meandering region having the area of at least 0.5 mm$^2$ is a first meandering region and the signal averaged over more than one adjacent segments of the microfluidic channel in the first meandering region is a first signal, wherein the first meandering region is in fluid communication with and positioned in series with respect to a second meandering region comprising a second microfluidic channel, and wherein the method comprises measuring a second signal averaged over more than one adjacent segments of the second microfluidic channel.

25. A method as in claim 1, wherein a first segment of the microfluidic channel in the meandering region is spaced apart from a second, adjacent segment of the microfluidic channel in the meandering region by a distance of less than the average width of the microfluidic channel in the meandering region.

26. A method as in claim 1, wherein a first segment of the microfluidic channel in the meandering region is spaced apart from a second, adjacent segment of the microfluidic channel in the meandering region by a distance of less than 2 times the average width of the microfluidic channel in the meandering region.

27. A method as in claim 1, comprising flowing in series in the microfluidic channel a predetermined sequence of fluid plugs including first, second and third fluids, wherein the first and second fluids are separated by the third fluid which is immiscible with both the first and second fluids.

28. A method as in claim 27, wherein the first and second fluids are liquids and the third fluid is a gas.

29. A method as in claim 28, wherein the first and/or second fluids is a rinse solution.

30. A method as in claim 29, wherein the first fluid is a rinse solution and the second fluid is a metal solution.

31. A method as in claim 8, wherein a first segment of the microfluidic channel in the meandering region is spaced apart from a second, adjacent segment of the microfluidic channel in the meandering region by a distance of less than 2 times the average width of the microfluidic channel in the meandering region.

32. A method as in claim 15, wherein a first segment of the microfluidic channel in the meandering region is spaced apart from a second, adjacent segment of the microfluidic channel in the meandering region by a distance of less than 2 times the average width of the microfluidic channel in the meandering region.

33. A method as in claim 1, wherein the signal is substantially homogeneous over more than one adjacent segments of the microfluidic channel.

34. A method as in claim 8, comprising measuring a signal from the meandering region, wherein the signal is substantially homogeneous over more than one adjacent segments of the microfluidic channel in the meandering region.

35. A method as in claim 15, comprising measuring a signal from the meandering region, wherein the signal is substantially homogeneous over more than one adjacent segments of the microfluidic channel in the meandering region.

36. A method as in claim 35, wherein the signal is a light transmittance signal.

37. A method as in claim 24, wherein the first signal is substantially homogeneous over all of the segments of the microfluidic channel in the first meandering region.

38. A method as in claim 1, wherein the exposing step involves exposing at least 50% of the area of the meandering region to light.

* * * * *